US010221445B2

(12) United States Patent
Beller et al.

(10) Patent No.: US 10,221,445 B2
(45) Date of Patent: Mar. 5, 2019

(54) CELL- OR VIRUS SIMULATING MEANS COMPRISING ENCAPSULATED MARKER MOLECULES

(75) Inventors: Katharina Beller, Hilden (DE); Thomas Doedt, Hilden (DE); Dirk Heckel, St. Martin d'Uriage (FR); Rainer Söller, Hamburg (DE)

(73) Assignees: QIAGEN GmbH, Hilden (DE); QIAGEN Hamburg GmbH, Hamburg (DE)

( * ) Notice: Subject to any disclaimer, the term of this patent is extended or adjusted under 35 U.S.C. 154(b) by 90 days.

(21) Appl. No.: 14/238,301

(22) PCT Filed: Aug. 13, 2012

(86) PCT No.: PCT/EP2012/003448
§ 371 (c)(1),
(2), (4) Date: Feb. 11, 2014

(87) PCT Pub. No.: WO2013/020714
PCT Pub. Date: Feb. 14, 2013

(65) Prior Publication Data
US 2014/0248606 A1    Sep. 4, 2014

(30) Foreign Application Priority Data
Aug. 11, 2011   (EP) .................................. 11006617

(51) Int. Cl.
| A61K 38/00 | (2006.01) |
| A61K 39/395 | (2006.01) |
| A61K 9/14 | (2006.01) |
| C07K 14/00 | (2006.01) |
| C12Q 1/6811 | (2018.01) |
| C12Q 1/6806 | (2018.01) |
| C12Q 1/6848 | (2018.01) |

(52) U.S. Cl.
CPC .......... C12Q 1/6811 (2013.01); C12Q 1/6806 (2013.01); C12Q 1/6848 (2013.01)

(58) Field of Classification Search
CPC ......... A61L 31/18; A61L 31/16; B82Y 15/00; B82Y 20/00; C12Q 2545/113
See application file for complete search history.

(56) References Cited

U.S. PATENT DOCUMENTS

| 4,638,045 A | 1/1987 | Kohn et al. |
| 4,806,621 A | 2/1989 | Kohn et al. |
| 4,946,929 A | 8/1990 | D'Amore et al. |
| 5,010,167 A | 4/1991 | Ron et al. |
| 5,019,379 A | 5/1991 | Domb et al. |
| 5,399,665 A | 3/1995 | Barrera et al. |
| 5,512,600 A | 4/1996 | Mikos et al. |
| 5,514,378 A | 5/1996 | Mikos et al. |
| 5,677,124 A | 10/1997 | DuBois et al. |
| 5,696,175 A | 12/1997 | Mikos et al. |
| 5,716,404 A | 2/1998 | Vacanti et al. |
| 5,736,372 A | 4/1998 | Vacanti et al. |
| 5,770,417 A | 6/1998 | Vacanti et al. |
| 5,804,178 A | 9/1998 | Vacanti et al. |
| 5,837,752 A | 11/1998 | Shastri et al. |
| 5,902,599 A | 5/1999 | Anseth et al. |
| 6,095,148 A | 8/2000 | Shastri et al. |
| 6,123,727 A | 9/2000 | Vacanti et al. |
| 6,132,773 A * | 10/2000 | Amiche ................. A01N 25/26 424/403 |
| 6,998,115 B2 | 2/2006 | Langer et al. |
| 2006/0240456 A1* | 10/2006 | Chen ...................... B82Y 15/00 435/6.11 |
| 2009/0253901 A1 | 10/2009 | Grinberg |

FOREIGN PATENT DOCUMENTS

| EP | 1 001 044 A2 | 5/2000 |
| WO | 99/47252 A2 | 9/1999 |
| WO | 99/47253 A1 | 9/1999 |
| WO | 02/077271 A2 | 10/2002 |
| WO | WO2004063387 * | 7/2004 |
| WO | 2007/111639 A1 | 10/2004 |
| WO | 2006/080849 A2 | 8/2006 |
| WO | 2007/031345 A2 | 3/2007 |
| WO | 2007/038763 A1 | 4/2007 |
| WO | WO2007111639 * | 10/2007 |
| WO | 2007/140402 A1 | 12/2007 |
| WO | 2008/030253 A2 | 3/2008 |
| WO | 2008/060557 A2 | 5/2008 |

OTHER PUBLICATIONS

Little, MIT, 2006, Thesis (Ph. D.)—Massachusetts Institute of Technology, Dept. of Chemical Engineering:pdf pp. 1-152.*
Barrera et al., "Synthesis and RGD Peptide Modification of a New Biodegradable Copolymer: Poly(lactic acid-co-lysine)," *J. Am. Chem. Soc.* 115:11010-11011, 1993.
Beld et al., "Highly Sensitive Assay for Detection of Enterovirus in Clinical Specimens by Reverse Transcription-PCR with an Armored RNA Internal Control," *Journal of Clinical Microbiology* 42(7):3059-3064, 2004.
Doty et al., "Development and validation of an independent positive control for nucleic acid tests for microorganisms that cause septicemia," Abstracts—Sixth International Symposium on Molecular Diagnostics, *Clinical Chemistry and Laboratory Medicine* 44(4), 2006.
Kwon et al., "Pseudopoly(amino acids): A Study of the Synthesis and Characterization of Poly(trans-4-hydroxy-N-acyl-L-proline esters)," *Macromolecules* 22:3250-3255, 1989.

(Continued)

*Primary Examiner* — Barry A Chestnut
(74) *Attorney, Agent, or Firm* — Seed IP Law Group LLP

(57) ABSTRACT

The present invention refers to a method, a composition and a kit for isolating biomolecules from any biological sample material containing cells, virus(es), microorganism(s) or a combination thereof comprising a cell- or virus-simulating means, wherein said cell- or virus-simulating means comprises at least one type of marker molecule(s), incorporated in at least one type of a layer, capsule, bead, sphere or particle, which is not a biological cell or provided on a substrate covered by a coating.

Figure 1:
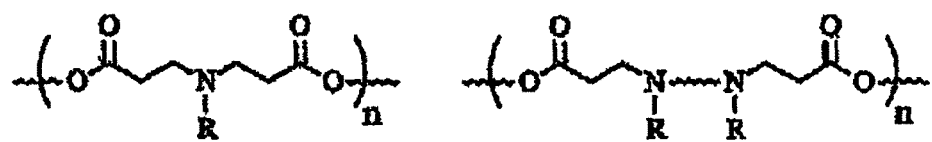

27 Claims, 2 Drawing Sheets
Specification includes a Sequence Listing.

(56) References Cited

OTHER PUBLICATIONS

Langer, "Selected advances in drug delivery and tissue engineering," *Journal of Controlled Release* 62:7-11, 1999.

Langer, "Biomaterials in Drug Delivery and Tissue Engineering: One Laboratory's Experience," *Acc. Chem. Res.* 33(2):94-101, 2000.

Lim et al., "A Self-Destroying Polycationic Polymer: Biodegradable Poly(4-hydroxy-L-proline ester)," *J. Am. Chem. Soc.* 121:5633-5639, 1999.

Lim et al., "Cationic Hyperbranched Poly(amino ester): A Novel Class of DNA Condensing Molecule with Cationic Surface, Biodegradable Three-Dimensional Structure, and Tertiary Amine Groups in the Interior," *J. Am. Chem. Soc.* 123:2460-2461, 2001.

Lynn et al., "Degradable Poly(β-amino esters): Synthesis, Characterization, and Self-Assembly with Plasmid DNA," *J. Am. Chem. Soc.* 122:10761-10768, 2000.

Putnam et al., "Poly(4-hydroxy-L-proline ester): Low-Temperature Polycondensation and Plasmid DNA Complexation," *Macromolecules* 32:3658-3662, 1999.

Uhrich et al., "Polymeric Systems for Controlled Drug Release," *Chem. Rev.* 99:3181-3198, 1999.

Wang et al., "A Novel Biodegradable Gene Carrier Based on Polyphosphoester," *J. Am. Chem. Soc.* 123:9480-9481, 2001.

Zhou et al., "Preparation of Poly(L-$_{serine\ ester}$): A Structural Analog of Conventional Poly(L-$_{serine}$)," *Macromolecules* 23:3399-3406, 1990.

Pasloske et al., "Armored RNA Technology for Production of Ribonuclease-Resistant Viral RNA Controls and Standards," *Journal of Clinical Microbiology* 36(12):3590-3594 (Dec. 1998).

\* cited by examiner

Ct values after PCR according to Example 1

Ct values after PCR according to Example 2

CELL- OR VIRUS SIMULATING MEANS COMPRISING ENCAPSULATED MARKER MOLECULES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 770025_455USPC_SEQUENCE_LISTING.txt. The text file is 1 KB, was created on May 20, 2014, and is being submitted electronically via EFS-Web.

The present invention refers to cell- or virus-simulating means, a method, a composition, an isolation device and a kit for isolating biomolecules from any biological material or microorganism(s) comprising said cell- or virus-simulating means, wherein said means encompasses at least one type of marker molecule(s), incorporated in at least one type of a layer, capsule, bead, sphere or particle, which is not a biological cell or provided on a substrate covered by a coating.

In modern nucleic acid-based or protein-based diagnostic methods several process steps like lysis, protein or nucleic acid extraction, nucleic acid amplification and detection of the biomolecule are involved before the diagnostic result is obtainable. In any of said process steps imperfections may occur. Therefore it is advantageous to be able to control the results of any or all of the processing steps, e.g. by comparison with detectable standards.

Detection and classification of bacterial, viral and fungal pathogens is critical for diagnosis and effective treatment of diseases such as sepsis or hospital acquired infections as MRSA (methicillin resistant *Staphylococcus aureus*). Today classical culturing methods are still widely used in order to determine the causative agent of an infection. The drawback of such methods is that they take up to several days until a pathogen is identified and that the rate of false negative results is relatively high. In addition the spread of pathogen strains which are resistant to commonly used antibiotics is growing which requires determination of resistances present in the infecting strains. Using classical microbiological methods these analyses are time-consuming and in most instances results are delivered too late for a therapeutic decision.

For transplantations of solid organs, infection with bacteria and fungi may pose a major problem. Special focus needs to be addressed to fungal infections in clinical setting because although the rate of fungal infections is lower compared to other pathogens, the mortality rate of invasive fungal infections is high. The most frequently detected fungal strains in transplantation recipients are *Candida* spp. and *Aspergillus* spp.

Modern molecular biological methods such as real time PCR have the potential to facilitate rapid, reliable and informative diagnosis of a wide range of bacterial, fungal and viral infections.

Increased numbers of genomic sequences of pathogens are available and are assessable for the design of diagnosis assays. Multiplex capacity of real time assays and platforms allow parallel detection of bacterial, viral and/or fungal strains, antibiotic resistances and control sequences.

Nevertheless, methods for isolation of bacterial, fungal and viral DNA which are the basis for molecular biological detection of the pathogens are far from being standardized. There are many different methods published to lyse bacterial and fungal cells and to extract DNA from the pathogen lysates. Many of those methods require time consuming and costly enzymatic treatments with lytic enzymes such as lysozyme, lysostaphin, lyticase and others. To prevent false negative results when using sensitive PCR based methods, it is necessary that the enzymes used to lyse the cells, the reagents that are used to isolate the DNA from the pathogens and the PCR reagents employed to amplify the sequences of interest are free of contaminating DNA. In addition the complete workflow of lysing pathogenic cells in human samples isolating the DNA, amplifying and detecting the relevant sequences should be monitored by adequate controls to confirm the validity of the diagnostic result.

Up to now there are mainly 3 systems available on the markets which address these needs to some extend:

One is for the diagnosis of pathogens responsible for sepsis whereas the others allow detection of MRSA. The first one, SeptiFast System from Roche, (http://www.roche.de/diagnostics/labor/lightcycler septifast.htm), allows detection of 25 different pathogens (bacteria and fungi) plus detection oft mecA resistance gene from blood samples. It is a complete CE-IVD marked workflow including lysis of pathogens, purification of DNA and detection in the Light Cycler Instrument.

The second one from Cepheid, Xpert MRSA (http://cepheid.com/sites/cepheid/content.cfm?id=253) is an automated DNA test for detecting MRSA from nasal swab specimens. Sample preparation, amplification and real-time detection are completely integrated. The Xpert MRSA assay is FDA cleared (510(k)).

The last system is the BD GeneOhm MRSA/StaphSR Assay (http://www.bd.com/geneohm/english/). This real time PCR assay is available for identification of *Staphylococcus aureus* (SA) and methicillin-resistant *Staphylococcus aureus* (MRSA) from patients colonized in the nasal passage and a second variant for direct detection from a whole blood sample from patients with positive blood cultures. The BD GeneOhm assays offer simple test procedures that provide results within two hours directly from blood or nasal swabs. The assay is easy to perform and requires less technologist time than traditional microbiology diagnostic tests, which can take two days to generate results. The analytical sensitivity is described as 2 cfu/PCR or 300 cfu/swab.

However all these systems are focused on special applications. A remaining need is to develop tools for controls of lysis of pathogens and sample preparation which can be equally used in other diagnostic test systems.

Further approaches to control nucleic acid treatment methods or nucleic acids based diagnostic workflows were the addition of free plasmid DNA or armoured RNA to the biological samples to control the nucleic acid isolation and processing. However, in the approach with free plasmid said control nucleic acid is isolated as well, if the cells of interest are not successfully lysed, whereas in the armoured RNA approach said full process control is restricted to RNA virus diagnostic assays.

In EP application with the application number EP-10 010 447.0 a method for nucleic acid isolation is described including an internal standard of beads whereon a pre-known amount of specific cells are attached. These cells are processed in the same way as the cells contained in a sample.

The object of the present invention was to provide a means and a method for allowing a concerted and purposeful release of a specific compound into a considered sample, and a method for controlling the efficiency of the release of a compound, e.g. to indicate the efficiency of a lysis procedure and the functionality of the specific diagnostic test.

This object is met by a cell- or virus-simulating means comprising at least one type of marker molecule(s) or compound(s) as defined in the claims, incorporated in at least one type of a layer, capsule, bead, sphere or particle, which is not a biological cell, or provided on a substrate covered by a coating, the methods and uses as defined in the claims, an isolating device usable in said methods and a kit for carrying out said methods.

In the present application the term "cell- or virus-simulating means" is used to describe any solid object or article comprising at least one type of marker molecule(s) or compound(s) incorporated in at least one type of a layer, capsule, bead, sphere or particle. The "cell- or virus simulating means" is not represented by a (complete) biological cell or organism, and not by a virus, a phage or phage core particle, without any artificial modification. However, the marker molecule(s) or compound(s) as such may be a (complete) biological cell or organism or fragments thereof, and in certain embodiments a virus, a phage or phage core particle, which is/are incorporated in at least one type of an artificial layer, capsule, bead, sphere or particle or provided on a substrate covered by a coating, which is able to release the marker molecule(s) or compound(s) by chemical or mechanical treatment. The term "cell-simulating" means that the solid object or article simulates any biological cell, wherein "cell" means any naturally occurring cell, including eukaryotic, in particular mammalian cells or prokaryotic cells, e.g. bacteria, yeast, cocci, fungi, algae, archaea etc. In certain embodiments the "cell- or virus-simulating means" does not completely simulate said cell or virus but has only properties similar to those of a cell or virus. For example the release of the marker molecule(s) or compound(s) from the cell- or virus-simulating means may actually be easier than it would be for the real cell or virus. In such a case the means may rather provide a protection like a protective shell for the marker molecule(s) or compound(s), e.g. against degradation, similar to but not mandatorily as strong as the protection a cell wall or a virus may provide.

Preferably the cell- or virus simulating means is an artificially prepared solid object or article, which means that said object or article is not naturally occurring. In particular it is not a biological cell, a biological organism, a virus a phage or a phage core particle but it may include such a biological cell, a biological organism, a virus, a phage or a phage core particle. Preferably either the core or the outer surface of the means comprises artificially prepared compounds not occurring in biological materials like a biological cell, a biological organism, a virus a phage or a phage core particle. The compounds used for the core, particularly for a solid core, and compounds usable for the layer/cover/coating of the marker molecules are described in detail below. Particularly preferred the cell- or virus simulating means comprises an artificial layer, capsule, bead, sphere or particle.

"Artificial" means that the considered subject has a composition not naturally occurring in biological systems, e.g. in a cell, a virus, a phage or a phage core particle. Preferably the artificial subject comprises at least one component of the templates for preparing the core or of the polymers (polyelectrolytes, polypeptides or polymers for polymersom preparation) described below for preparing the shell, cover, layer(s) or coating on the marker molecules of the cell- or virus simulating means, particularly preferred at least one of the polymers for preparing the shell, cover, layer(s) or coating on the marker molecules.

The term "marker molecule(s)" or "marker compound(s)" encompasses any detectable molecule or compound or a group of detectable molecules or compounds e.g. a dye or a fluorescent dye, a dye developing compound, an antigen or antibody, a radioactive molecule or compound or any of the biomolecules as defined below. The term "marker molecule" or "marker compound" shall also encompass a (complete) biological cell, a biological organism, in particular a bacterium, coccus and/or fungus, a virus, a phage or a phage core particle, which cell, organism, virus, phage or phage core particle contains one or more of such detectable molecules or compounds or groups of detectable molecules or compounds. At least one of said dye or fluorescent dye, a dye developing compound, an antigen or antibody, a radioactive molecule or compound as well can be used as a label in or on at least one of the biomolecules serving as a marker molecule. A preferred marker molecule is at least one of any of the biomolecules described below, wherein it is particularly preferred that the biomolecules include any pre-known sequence as defined below, any detectable label (e.g. at least one of them mentioned before) or they provide/develop any detectable signal after release from the cell- or virus-simulating means.

The detectable and/or the isolated biomolecule can be a macromolecule, particularly preferred the biomolecule is at least one type of nucleic acid(s) (the "types" of nucleic acids are preferably RNA or DNA) or an oligopeptide (up to 30 amino acids), a polypeptide (more than 30 up to 100 amino acids) or a protein (more than 100 amino acids). It is as well possible that more than one type of marker molecules are included in the cell- or virus-simulating means, e.g. a nucleic acid and/or a protein and at least one further marker molecule like a dye, a fluorescent dye, a dye developing compound, an antigen and antibody or similar, either as a label in/on the biomolecule or as a separate marker compound. A particularly preferred biomolecule is at least one type of a nucleic acid, which comprises a pre-known sequence, is labelled or both.

Nucleic acid(s) which can be either detected (used as the marker molecules) or isolated and/or purified using the method of the present invention include single- and double-stranded nucleic acids, straight-chain, branched or circular nucleic acids, in particular DNA and RNA, more particular genomic DNA (gDNA), plasmid DNA, DNA from organelles or fragments of the before-mentioned, PCR-fragments, cDNA, rRNA, mRNA, miRNA, siRNA, snRNA, tRNA, hnRNA or fragments of the before-mentioned as well as oligonucleotides and modified nucleic acids like e.g. so-called peptide or locked nucleic acids, respectively, (PNA or LNA) or ribozymes, and they may be of microbial, including viral, bacterial, coccal and fungi, or human, animal or plant origin. In addition, also hybrids formed of DNA and RNA can be purified, without being limited to the mentioned.

Oligopeptides, polypeptides or proteins according to the present invention are any naturally occurring or artificial amino acid sequences like e.g. hormones, signal peptides, structural proteins, enzymes, receptors, antibodies and any other peptide or protein of interest or any artificial peptide/protein.

If the nucleic acids or the peptide(s)/protein(s) serve as the marker-molecule(s) in the cell- or virus-simulating means according to the invention it is particularly preferred that said nucleic acids, peptides or proteins either have a pre-known sequence allowing the detection of said molecules by known techniques like e.g. PCR, sequencing, blotting methods, specific restriction, digestion or test probes, or they are labelled e.g. by a dye, a fluorescent dye, a dye-developing compound, green fluorescent protein (GFP)-linkage, radioactivity, an antigen or antibody or any other of the detectable markers known to skilled persons. Furthermore the detectable molecule can have a pre-known sequence and a label.

The cell- or virus-simulating means of the present invention can be used as a standard in a method for biomolecule release and/or isolation from a biological sample. Said cell- or virus-simulating means might be used either for finding and/or defining and/or establishing and/or controlling the conditions in a method suitable for effective biomolecule release or isolation. The standard might be used separate from the biological sample ("external standard") and is processed as intended for the biological sample but in parallel with the biological sample in a separate sample tube. The use of the cell- or virus-simulating means as an external standard may also result in a so called "full process control", in particular used for controlling the correct detection process of isolating the test specific pathogen(s). For this purpose the cell- or virus-simulating means is supposed to be equivalent to the target to be detected and/or isolated, i.e. preferably it should be equivalent to the pathogen. In such cases preferably the shell, cover, layer(s) or coating on the marker molecules may only be used to protect the incorporated cell, organism, virus, phage and/or phage core particle against attack and/or degradation. For this purpose it may be sufficient that the shell, cover, layer(s) or coating on the marker molecule is not as strong as in a corresponding cell, virus or phage. However, it is also possible to use a shell, cover, layer(s) or coating on the marker molecules which is as stable as the corresponding cell, virus or phage. Once the shell, cover, layer(s) or coating on the marker molecules is damaged and the interior, preferably the interior pathogen, is released, it may be treated in the same way as the biological sample which is treated in parallel.

In another embodiment, however, the cell- or virus-simulating means is used as an "internal standard", i.e. in the same sample processing tube/container as the biological sample from which the biomolecules of interest are released, isolated or purified. In the latter case, where an internal standard is used, it is clear that the marker molecule should differ in at least one property from the sample organism and/or biomolecule of interest isolated from the biological sample. Examples of such differences are the amino acid or nucleic acid sequence, detectable modifications of the sequence, the labelling profile or similar.

In particular the cell- or virus simulating means can be used to effect and to control the release of the enclosed or embedded marker molecule(s)/compound(s) or biomolecules both at a desired time and in a desired amount. The lysis/isolation conditions can be modified and adapted to obtain the desired result. The lysis/isolation conditions optimized by this control method can then be used to release and/or isolate a desired biomolecule from a biological sample, in particular from a sample which is mimicked by the used cell- or virus simulating means.

Furthermore the lysis conditions optimized for the release of the embedded or encapsulated molecules can be used to provide (a) desired molecule(s) at a pre-determined time point during any biological procedure. E.g. the cell- or virus-simulating means can be used for deliberate release of a marker molecule or a biomolecule into a liquid sample by chemical or mechanical lysis.

Suitable biological samples for biomolecule release or isolation are all biological samples comprising or consisting of intact or mortified cells or viruses. Preferred are cell-comprising or cell-free biological samples, such as, for example bodily fluids such as blood, plasma, serum, sperm, cerebrospinal fluid, saliva, sputum or urine, leukocyte fractions, buffy coats or faeces, surface biopsies, aspirates, lavages, skin fragments, entire organisms, organs and tissue of Metazoa, preferably of insects, birds, reptiles, amphibians, fishes, plants and mammals, in particular of humans, domestic animals or pets, or farm animals, for example in the form of autopsies, biopsies, fine-needle aspirates or tissue sections, isolated cells, for example in the form of adherent or suspended cell cultures, plants, parts of plants, plant tissue or plant cells, bacteria, viruses, yeast, cocci, fungi, algae and protozoans, encapsulated or enveloped biomolecules or liposomes.

The method for isolating any biomolecule(s) according to the present invention includes at least cell lysis or lysis of a non-cellular microorganism like e.g. a virus and optionally at least one of the following steps: sample preparation, biomolecule extraction, biomolecule concentration, biomolecule purification, reversal transcription, nucleic acid amplification and detection of the isolated biomolecules. Preferably the method includes at least cell lysis, amplification and detection of the biomolecules.

In particular the method of the present invention can for example be used to determine any infection of viruses or cellular microorganism(s) in samplings or remains of any living organism (mammal, bird, reptile, amphibians, fish or plant); samples comprising (desired) fungi or microorganism as e.g. algae, fungi, protozoans, or bacteria, viruses or virus particles, e.g. cultures of said organisms, optionally contaminated by undesired fungi or microorganism as mentioned before, including mycoplasma, viruses and/or virus particles; any natural or artificial product (such as beverage(s), food or food compounds optionally contaminated with possible detrimental organisms, viruses or phages) or any traces of such samplings, remains, natural or artificial products. To diagnose such viral or microorganism(s) infection any body tissue or body fluid, cell sample, plant sample, excrement, food product, food compound, cultural media or fluids, or traces of it, comprising the virus(es) or microorganism(s) can be used as the (biological) sample. Further the method of the present invention can be used to determine whether any sample is contaminated with at least one microorganism, e.g. drinking water contamination (in tap water or reservoir), contamination of fresh water (artesian river, stream or lake), seawater (particularly fish farms) or food contamination. The microorganism is preferably selected from at least one bacterium, fungus, yeast, alga, virus, protozoan or coccus or of any mixture of them.

According to one preferred embodiment of the present invention the cell- or virus-simulating means is used as an internal standard present during the whole biomolecule isolation and/or analysing method and is treated exactly the same way and under the same conditions as the sample containing the biomolecule of interest, e.g. the biomolecule-containing microorganisms. Accordingly the quantity and/or quality of a biomolecule isolation e.g. from the microorganisms or the virus can be estimated by comparison of the yield or quality of the isolated marker molecules of the internal standard with the optimal yield or quality obtainable from said internal standard under the applied conditions. In particular by using the internal standard of the present invention each of the processing steps, including the lysis of the cells can be controlled.

The biomolecule serving as a marker molecule in the cell- or virus-simulating means is preferably a nucleic acid or an oligopeptide, a polypeptide or a protein having an at least partially pre-known sequence. The nucleic acid sequence as well as the peptide sequence contained in the cell- or virus-simulating means comprises preferably at least 10, preferably at least 15, more preferred at least 30 bases (RNA), base pairs (bp) (DNA) or amino acids (peptides/proteins), respectively, which are known ("pre-known sequence"), allowing the detection of the biomolecule after the isolation. It is further preferred that the whole sequence of the biomolecule provided with the cell- or virus-simulating means is known. A particular preferred biomolecule is a nucleic acid sequence comprising at least 50 bases/bp, more preferred at least 100 bases/bp, and even more preferred at least 200 bases/bp. A particularly preferred nucleic acid is a PCR product having a defined length like e.g. in the range of for example 300 to 1000 bp. Another preferred embodiment is an oligopeptide, a polypeptide or a protein e.g. with up to 500 amino acids. It is particularly preferred that the whole sequence of the biomolecule is pre-known.

In a further preferred embodiment independent from the pre-known sequence, but possibly as well in combination therewith, the biomolecule serving as a marker molecule in the cell- or virus-simulating means can be a labelled biomolecule, selected from them as described above. A particularly preferred labelled molecule is a dye- or fluorescent dye-labelled nucleic acid, oligopeptide, polypeptide or protein or a GFP-labelled peptide or protein. Furthermore the green fluorescent protein (GFP) itself can serve as a marker molecule. Another preferred embodiment is the labelling of the marker-molecule with a dye-developing molecule, e.g. any of the known molecules developing a dye/fluorescence under defined conditions or in contact with a substrate.

In particular if the cell- or virus simulating means is used as an "external standard" it is preferred that the means comprises a labelled nucleic acid, peptide or protein sequence, wherein the before-mentioned labels are particularly preferred.

The cell- or virus-simulating means of the present invention is built up in a way that it simulates the composition or construction, respectively, of a biomolecule containing sample, in particular a cell or a virus. More in detail the means comprises at least one type of a marker molecule, preferably at least (a) biomolecule(s) with an at least partially pre-known sequence or any label, allowing to detect said biomolecule after isolation and processing. The at least one type of marker molecule included in the standard according to the invention can be used to control quality and/or quantity of the biomolecule isolation and processing from a biological sample. It is particularly preferred that the sequence of the marker molecule provided with the standard, in particular with the internal standard, is one which is not estimated to be found as well in the sample to be analysed. This means that either a marker molecule type is used which usually is not present in the considered biological sample (e.g. a dye, a fluorescent dye, a dye developing compound, an antigen etc.) or, if a biomolecule is used, the biomolecule sequence of the internal standard should preferably differ clearly from the biomolecule sequences contained in the sample to allow the qualitative and quantitative analysis of the biomolecule of the standard as well as of the sample biomolecules independent from each other. In particular when being used as an external standard, it may be preferred that the sequence of the marker molecule is estimated to be identical to the one found as well in the sample to be analysed. The biomolecules "differ clearly" from each other, if they either share less than 20 amino acids or less than 20 bases/bp in the same order within the sequence, preferably less than 15, more preferred less than 10 and even more preferred less than 5, or, if they share more than 5, 10, 15 or 20 amino acids or nucleic acids in the same order, an obtainable PCR product with a defined primer pair shows different results (e.g. different length of the product), or the polypeptides or proteins have as a whole a different sequence, like e.g. different splice variants of a protein. Even in the last case, where more than 5, 10, 15 or 20 amino acids or nucleic acids are shared in the same order, the whole sequence should share not more than 50% of the same sequence.

If on the other hand the same sequences of a peptide/protein or nucleic acid sequence have to be used, which as well can be expected from the isolated biomolecules, the biomolecule(s) of the standard preferably differ(s) from the isolated biomolecule by a labelling pattern. Of course the biomolecules used in the standard can differ from the isolated biomolecules as well in the sequence and the labelling pattern.

With "processing" of the biomolecule containing sample or the biomolecule itself according to the present application is meant any treatment or step applied to the biomolecules containing sample or the biomolecules itself after extraction from their natural or artificial environment, like e.g. purification, enrichment, lysis, mechanical disruption, amplification, hybridization, restriction, sequencing, blotting, labelling or similar.

The cell- or virus-simulating means usable as the standard is provided either in form of a capsule, bead, sphere or particle, preferably having a regular or irregular shape with an average diameter of 0.1 to less than 100 µm, more preferably 0.5 to 50 µm, most preferably in a size of a bacterial or fungal cell, particularly 1 to 10 µm, or it is provided in form of a coating or layer on the inner surface of a device suitable for use in a biomolecules isolation method. In both cases the marker molecules of the standard are provided in a known amount and in both cases they are covered by at least one layer, preferably more than one layer, more preferably 2 and up to 100 layers and particularly preferred more than 2 and up to 10 or up to 20 or up to 30 layers of an assembling, preferably a self-assembling material.

In a first possible embodiment the marker molecules are comprised in a core of a capsule, bead, sphere or particle wherein the capsule, bead, sphere or particle further has a cover or a shell covering said core at least partially, preferably encompassing the core. The core may essentially consist of the marker molecules, optionally dissolved in a suitable liquid further optionally comprising stabilizing agents, buffering agents or similar, or it may comprise further ingredients like e.g. solid or porous inorganic or organic materials (templates), whereon the molecules are applied, or any other suitable composition. Preferably the core comprises a template.

In a second embodiment the marker molecules are adsorbed or applied to an inner surface of a device which suitably can be used for biomolecules isolation from biological samples. Such a device can be for example a tube, a cup like an Eppendorf cup, a multiwell plate a spin column tube or anything similar wherein the biological sample can be treated, preferably any biological cell or microorganism can be lysed. The molecules applied or adsorbed to the inner surface of the device are covered by at least one layer or a coating of the assembling, preferably a self-assembling material.

In both embodiments the layer(s), cover, coating or shell covering the marker molecules are protecting the molecules against any unintended dissolution. Said layer(s), cover, coating or shell, however, are designed in a way that under defined conditions, in particular under conditions suitable for lysis of interesting cells or viruses within the biological sample, the protecting structure decomposes and the marker molecules dissolve into the lysis solution.

Biological cells or viruses from various biological samples can be lysed in different ways. Dependent on the type of cell or virus of interest it might be in some cases preferable to lyse the cells or viruses by chemical or enzymatic lysis and in other cases by mechanical lysis and in some cases by a mixture of both. In particular if a biological sample comprises different types of cells or viruses it is preferable that the marker molecules of the standard are only released when the cells of interest or the virus as well are lysed. Accordingly it is particularly preferred that the cell- or virus simulating means is designed in a way that it is inert against any conditions not representing lysis conditions of cells or virus of interest, but releases the contained marker molecules under conditions suitable for lysis of the interesting cells or viruses. For example, if the standard shall be used to control the lysis of cells which are lysed by mechanical lysis the protecting layer(s), cover, coating or shell shall be as well decomposable by mechanical lysis, however, preferably should resist any chemical or enzymatic lysis step. In particular in case that a chemical and/or enzymatic pre-lysis e.g. of red blood cells takes place before the mechanical lysis step is carried out, the cell- or virus-simulating means should resist the chemical and/or enzymatic pre-lysis and only be lysed by the mechanical lysis step. A resistance against chemical or enzymatic lysis may be provided e.g. by crosslinking or covering the last layer of the assembling material. On the other hand, if cells or viruses of interest are lysable by chemical lysis, e.g. by chaotropic salt containing lysis buffers, the protecting layer(s), cover, coating or shell as well shall be decomposed by the same chemical lysis and marker molecules of the cell- or virus-simulating means preferably shall be released.

The cell- or virus simulating means can be designed to simulate any particular cell or virus of interest. If for example a cell has a thick cell wall it is preferred to design the means similar to the cell constitution, e.g. by providing a thick coating or shell covering the marker molecules of the standard. Such cells and standards preferably are lysed by mechanical lysis. If on the other hand the cell of interest has a thin cell wall or membrane and said cell or a virus can be lysed by lysis with a lysis buffer essentially without any mechanical impact, the standard can provide the marker molecules, e.g. nucleic acids, covered only with a thin coating, e.g. consisting of only several layers of a chemically de-assembling or decomposing material. The means preferably simulates the cells or viruses of interest as well in view of their behaviour during lysis. They further may be adapted to several particular lysis conditions.

The assembling, preferably self-assembling material forming the layer(s), cover, coating or shell preferably is selected from polyelectrolytes known in the art for preparation of layer-by-layer coatings, polymers used for polymersom preparation, polypeptides designed for the preparation of thin layers, phospholipids suitable for liposome preparation and any further material which is able to form layers which are chemically or mechanically disintegratable under conditions not negatively affecting biological macromolecules like e.g. nucleic acids or proteins.

The decomposition is characterized by the substantially sequential disintegration or detachment or degradation of at least a portion of the polyelectrolyte layers that make up the coating. The decomposition may be at least partially hydrolytic, at least partially enzymatic, at least partially thermal, at least partially mechanical and/or at least partially photolytic. The coatings can comprise at least one layer of the before mentioned materials and up to 100 layers and is preferably between about 0.1 nm and about 100 nm thick.

The term "polyelectrolyte" as used herein, refers to a polymer which under some set of conditions (e.g., physiological conditions) has a net positive or negative charge. Polycations have a net positive charge and polyanions have a net negative charge. The net charge of a given polyelectrolyte may depend on the surrounding chemical conditions, e.g., on the pH.

A polyelectrolyte coating comprises layers of polycationic and polyanionic compounds. The polycationic compound can be selected from polyamine such as, for example, a polypeptide, polyvinyl amine, poly(aminostyrene), poly (aminoacrylate), poly(N-methyl aminoacrylate), poly(N-ethylaminoacrylate), poly(N,N-dimethyl aminoacrylate), poly(N,N-crosmarmelose diethylaminoacrylate), poly (aminomethacrylate), poly(N-methylamino-methacrylate), poly(N-ethyl aminomethacrylate), poly(N,N-dimethyl aminomethacrylate), poly(N,N-diethyl aminomethacrylate), poly(ethyleneimine), poly(diallyl dimethylammonium chloride), poly(N,N,N-trimethylaminoacrylate chloride), poly (methyacrylamidopropyltrimethyl ammonium chloride), chitosan and combinations comprising one or more of the foregoing polycationic materials.

The polyanionic can be selected e.g. from a polypeptide, alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose, acidic polysaccharides, croscarmelose, synthetic polymers and copolymers containing pendant carboxyl groups, and combinations comprising one or more of the foregoing polyanionic materials.

Any decomposable or degradable polyelectrolyte can be used in a thin film of the present invention, including, but not limited to, hydrolytically decomposable or degradable, bio decomposable or degradable, thermally decomposable or degradable, and photolytically decomposable or degradable polyelectrolytes. Hydrolytically decomposable or degradable polymers known in the art include for example, certain polyesters, polyanhydrides, polyorthoesters, polyphosphazenes, and polyphosphoesters. Biodegradable polymers known in the art, include, for example, certain polyhydroxyacids, polypropylfumerates, polycaprolactones, polyamides, poly(amino acids), polyacetals, polyethers, bio decomposable or degradable polycyanoacrylates, bio decomposable or degradable polyurethanes and polysaccharides. For example, specific bio decomposable or degradable polymers that may be used in the present invention include but are not limited to polylysine, poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Those skilled in the art will recognize that this is an exemplary, not comprehensive, list of biodegradable polymers. The properties of these and other polymers and methods for preparing them are further described in the art. See, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. Nos. 4,806,621; 4,638,045 to Kohn; and U.S. Pat. No. 4,946,929 to d'Amore; see also Wang et al, J. Am. Chem. Soc. 123:9480, 2001; Lim et al., J. Am. Chem. Soc. 123:2460, 2001; Langer, Ace. Chem. Res. 33:94, 2000; Langer, J. Control Release 62:7, 1999; and Uhrich et al., Chem. Rev. 99:3181, 1999. Of course, copolymers, mixtures, and adducts of these polymers may also be employed. The anionic polyelectrolytes may be decomposable or degradable polymers with anionic groups distributed along the polymer backbone. The anionic groups, which may include carboxylate, sulfonate, sulphate, phosphate, nitrate, or other negatively charged or ionizable groupings, may be disposed upon groups pendant from the backbone or may be incorporated in the backbone itself. The cationic polyelectrolytes may be decomposable or degradable polymers with cationic groups distributed along the polymer backbone. The cationic groups, which may include protonated amine, quaternary ammonium or phosphonium derived functions or other positively charged or ionizable groups, may be disposed in side groups pendant from the backbone, may be attached to the backbone directly, or can be incorporated in the backbone itself. For example, a range of hydrolytically degradable amine containing polyesters bearing cationic side chains have recently been developed (Putnam et al. Macromolecules 32:3658-3662, 1999; Barrera a/. J. Am. Chem. Soc. 115:11010-11011, 1993; Kwon et al. Macromolecules 22:3250-3255, 1989; Lim et al. J. Am. Chem. Soc. 121:5633-5639, 1999; Zhou et al. Macromolecules 23:3399-3406, 1990; each of which is incorporated herein by reference). Examples of these polyesters include poly(L-lactide-co-L-lysine) (Barrera et al. J. Am. Chem. Soc. 115:11010-11011, 1993; incorporated herein by reference), poly(serine ester) (Zhou et al. Macromolecules 23:3399-3406, 1990; which is incorporated herein by reference), poly(4-hydroxy-L-proline ester) (Putnam et al. Macromolecules 32:3658-3662, 1999.; Lim et al. J. Am. Chem. Soc. 121:5633-5639, 1999; each of which is incorporated herein by reference), and more recently, poly[a-(4-aminobutyl)-L-glycolic acid].

In addition, poly(beta-amino ester)s, prepared from the conjugate addition of primary or secondary amines to diacrylates, are suitable for use with the invention. Typically, poly(beta-amino ester)s have one or more tertiary amines in the backbone of the polymer, preferably one or two per repeating backbone unit. Alternatively, a co-polymer may be used in which one of the components is a poly(beta-amino ester). Poly(beta-amino ester)s are described in U.S. Ser. No. 09/969,431, filed Oct. 2, 2001, entitled "Biodegradable poly(beta-amino esters) and uses thereof and Lynn et al., J. Am. Chem. Soc. 122:10761-10768, 2000, the entire contents of both of which are incorporated herein by reference.

Exemplary poly(beta-amino ester)s are shown in FIG. 1. Exemplary R groups include hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups.

Exemplary linker groups A and B include carbon chains of 1 to 30 carbon atoms, heteroatom-containing carbon chains of 1 to 30 atoms, and carbon chains and heteroatom-containing carbon chains with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups. The polymer may include, for example, between 5 and 10,000 repeat units.

Preferred members of the group of polyanions are polyphosphates, polysulphates, polysulphonates, polyvinylsulphonates, polyphosphonates, polyvinylphosphonates and poly(meth)acrylates; preferred members of the group of polykations are polyethyleneimine, polyvinylamine and polyvinylpyridine. Preferred members of the group of biopolymers are alginic acid, gum arabicum, pectins, proteins, carboxymethylcellulose (CMC), chitosane, chitosane sulphate or lignin sulphonate.

Alternatively, zwitterionic polyelectrolytes may be used. Such polyelectrolytes may have both anionic and cationic groups incorporated into the backbone or covalently attached to the backbone as part of a pendant group. Such polymers may be neutrally charged at one pH, positively charged at another pH, and negatively charged at a third pH. For example, a film may be deposited by LBL deposition using dip coating in solutions of a first pH at which one layer is anionic and a second layer is cationic. If the film is put into a solution having a second different pH, then the first layer may be rendered cationic while the second layer is rendered anionic, thereby changing the charges on those layers.

The composition of the polyanionic and polycationic layers can be fine-tuned to adjust the degradation rate of each layer within the film. For example, the degradation rate of hydrolytically degradable polyelectrolyte layers can be decreased by associating hydrophobic polymers such as hydrocarbons and lipids with one or more of the layers. Alternatively, the polyelectrolyte layers may be rendered more hydrophilic to increase their hydrolytic degradation rate. In certain embodiments, the degradation rate of a given layer can be adjusted by including a mixture of polyelectrolytes that degrade at different rates or under different conditions. In other embodiments, the polyanionic and/or polycationic layers may include a mixture of degradable and non-degradable polyelectrolytes. Any non-degradable polyelectrolyte can be used with the present invention. Exemplary non-degradable polyelectrolytes that could be used include poly(styrene sulfonate) (SPS), poly(acrylic acid) (PAA), linear poly(ethylene imine) (LPEI), poly(diallyldimethyl ammonium chloride) (PDAC), and poly(allylamine hydrochloride) (PAH).

Alternatively or additionally, the degradation rate may be fine-tuned by associating or mixing non-biodegradable, yet biocompatible polymers (polyionic or non-polyionic) with one or more of the polyanionic and/or polycationic layers. Suitable nonbiodegradable, yet biocompatible polymers are well known in the art and include polystyrenes, certain polyesters, non-biodegradable polyurethanes, polyureas, poly(ethylene vinyl acetate), polypropylene, polymethacrylate, polyethylene, polycarbonates, and poly(ethylene oxide)s. Furthermore, because the thin film is produced in a layer-by-layer fashion, the composition of individual layers may be varied to tailor the degradation rate of various portions of the film. For example, the upper layers of the film, closer to the surface, may be adjusted to degrade faster than the layers of the film closer to the template, or vice versa. Depending on the thickness of the film, layer or coating the degradation rate within the film, layer or coating may be varied cyclically (e.g., for periodic release). Additionally or alternatively, the upper layers of the film, layer or coating, closer to the surface, may be adjusted to degrade under a first set of conditions (e.g., endosomal conditions) while the layers of the film, layer or coating that are closer to the template are adjusted to degrade under a second set of conditions (e.g., physiological conditions). In some embodiments, the various layers of the film, layer or coating may be modified to control the diffusion of materials within the film, layer or coating. For example, the released entity may be one that does not readily diffuse through the layers of the film, layer or coating.

Alternatively or in addition, bilayers may be covalently cross-linked, in particular the surface bilayers, to increase resistance of the film, layer or coating against chemical decomposition. For example, a bilayer of two polymers of opposite charge may be cross-linked thermally or by other mechanisms. Thermal cross-linking may be achieved by heating the film, layer or coating for a particular period of time. Chemical cross-linking may be achieved e.g. by exposing a film to UV light. For example, polymers having double bonds in or pendant to the backbone may be employed in the thin film, layer or coating and cross-linked after deposition. In another embodiment, reactive groups such as carboxyl, thiol, amine, hydroxyl, or halogen may be exploited to covalently cross-link films, layers or coatings. These groups may be made more reactive by methods known to those of skill in the art, for example, using carbodiimides or other groups such as isocyanates, 3-[(2-aminoethyl)dithio]propionic acid, and succinimidyl 4-[N-maleimidomethyl]cyclohexane-1-carboxylate (SMCC), that provide additional reactivity and good leaving groups. Additional groups that are suitable for cross-linking will depend on the composition of the various layers, as will be understood by those of skill in the art. A variety of cross-linking agents are available from Pierce Biotechnologies, Rockford, Ill. Such a cross-linking of the layer(s), in particular of the layers on the outer surface of the coating results in an increased resistance of the standard against chemical lysis.

For preparation of the cell- or virus simulating means the polyelectrolytes are applied on the marker molecules of the means (wherein nucleic acids themselves represent as well polyelectrolytic molecules). For preparation of the capsules, bead, spheres or particles according to the first embodiment of the present invention cited above the polyelectrolytes preferably are applied on a template. Said template either includes the marker molecules of the means or said marker molecules are applied to its surface.

A variety of materials can be used as templates for the application or adsorption of the marker molecules of the cell- or virus simulating means such as, but not limited to, metals, e.g., gold, silver, platinum, and aluminum; metal-coated materials; metal oxides; plastics; ceramics; silicon; glasses; $CaCO_3$; salt crystals; mica; graphite; hydrogels; and polymers such as polymer latices or melamine-formaldehyde particles; polyamides, polyphosphazenes, polypropylfumarates, polyethers, polyacetals, polycyanoacrylates, polyurethanes, polycarbonates, polyanhydrides, polyorthoesters, polyhydroxyacids, polyacrylates, ethylene vinyl acetate polymers and other cellulose acetates, polystyrenes, poly(vinyl chloride), poly(vinyl fluoride), poly(vinyl imidazole), poly(vinyl alcohol), poly(ethylene terephthalate), polyesters, polyureas, polypropylene, polymethacrylate, polyethylene, poly(ethylene oxide)s and chlorosulphonated polyolefins; and combinations thereof. For example, a template of one material may be coated with a second material, or two materials may be combined to form a composite. Lipid vesicles or emulsion droplets are likewise suitable.

Template particles which are preferred are comprising, preferably consisting of $CaCO_3$, aluminosilicates, silicates, polymer latices like polystyrene or styrene copolymers, melamine-formaldehyde particles or. The size of the template particles can be up to 50 μm. However, in most cases, the template particles are up to 10 μm, particularly preferably from 5 nm to 5 μm, in size. The shape of the template particles is not critical. Both spherical and anisotropic particles can be coated.

For the application of the marker molecules and the polyelectrolyte layers to the template preferably a dispersion of the template particles in an aqueous solution is produced. As a first application the marker molecules are adsorbed to the template. A further possibility is that the marker molecules are incorporated into the template, in particular if the template is porous. Polyelectrolyte molecules from which the first layer is to be built up are then added to this dispersion. These polyelectrolyte molecules may have the same or the opposite charge as the surface of the template particles. The amount of the added polyelectrolyte molecules is chosen so that all the material is required for building up the first layer, or an excess is used. In the latter case, removal of the excess polyelectrolyte molecules not required to build up the first layer is expedient before addition of oppositely charged polyelectrolyte molecules for building up the second layer. The polyelectrolyte molecules can be removed by known methods, in particular centrifugation, filtration or/and dialysis. Removal by membrane filtration as described hereinafter is particularly preferred. Subsequently there is further alternate application of oppositely charged layers of polyelectrolyte molecules, it being possible to choose for each layer with the same charge identical or different polyelectrolyte species or mixtures of polyelectrolyte species. The number of layers can in principle be chosen as desired.

It is also possible to employ aggregates of subparticles as initial cores (template particles) for coating with polyelectrolytes. These aggregates can, where appropriate, be employed in the preshaped or preformed state. Such a preforming can be achieved, for example, by applying external electrical direct or/and alternating fields or magnetic fields to suspensions with subparticles. The shape of the capsules can be determined by preshaped aggregates. It is additionally possible to obtain such aggregates with a great uniformity with regard to the size distribution (monodispersity). However, non-preshaped aggregates are also just as suitable. Spherically shaped aggregates are of particular interest.

The template particles used do not necessarily have to be charged in order to make application of the marker molecules or self-assembly of polyelectrolyte layers possible. On the contrary, it is possible to apply to uncharged cores a charged precursor film which is bound to the template particles by other interactions, for example hydrophobic interactions. After application of the required number of polyelectrolyte layers, the template can, if desired, be disintegrated, in particular comminuted or disaggregated. This results in capsules with a core comprising the marker molecules and a polyelectrolyte shell. The disaggregation of the template particles is carried out under conditions in which the marker molecules and the shells remain intact. A disaggregation can take place, for example, thermally or chemically depending on the material chosen for the template particles. The low molecular weight core ingredients produced in the disaggregation can reach the outside through the pores in the shell. This results in capsules with polyelectrolyte shells which contain nucleic acids in the core. Other coating substances can be applied to the polyelectrolyte molecules.

It is possible after disintegration of the template particles for a liquid phase to be present inside the capsule shell. It is possible in principle for the capsules to contain any liquid in their interior, for example an aqueous liquid, in particular an aqueous buffer solution or water. If it is intended to disintegrate the template after shell or coating preparation it is preferred to employ either $CaCO_3$ or partially crosslinked melamine-formaldehyde particles as template particles which can be disaggregated by adjusting the pH in the medium containing the enveloped particles to an acidic value, for example less than or equal to 1.5, while the shell layer itself remains intact. The partially crosslinked melamine-formaldehyde particles can also be disaggregated by chemical reactions, in particular by sulfonation in aqueous media. The sulfonating agents preferably used are alkali metal sulfates, alkali metal hydrogen sulfites and other water-soluble salts of sulphurous acid. Other preferred examples of template particles which can be disaggregated are soluble polymer cores, for example urea-formaldehyde particles, or salt crystals.

The fragments formed on disintegration of the template particles, for example in the case of partially crosslinked melamine-formaldehyde particles the oligomers produced on disaggregation, can escape from the interior of the capsules to the outside through pores, in particular nanopores, in the shell wall. They can then, if required, be removed from the capsules. This removal can be carried out by methods known to the skilled worker, for example by dialysis, filtration or/and centrifugation.

If it is intended to use particles having a solid core it is preferred to use compact solid or porous templates not disintegrating under the conditions used during commonly known biomolecule isolation conditions. Such template materials are mentioned above and are preferably organic polymers like polyacrylic acid, silicate, aliminosilicate, glass, metal or similar inert materials. If the template is not disintegrated it is particularly preferred that the marker molecules of the cell- or virus simulating means are not incorporated into the templates, but are adsorbed or applied to their surface. If the template is porous, the marker molecules as well can be inside of the pores, however, are still on a surface of the template. In case that a porous template is used, it is preferred that the pores have an average diameter of 0.3 to 30 nm, preferably 0.8 to 10 nm.

Polymers commonly used for polymersom preparation as well can be used to prepare the layer(s), coating, cover or shell of the cell- or virus simulating means of the present invention. Examples for such polymers for preparation of polymersomes are apmphiphilic polymers and can be selected from diblock copolymer polystyrene-b-poly(L-isocyanoalanine(2-thiophen-3-yl-ethyl)amide) (PS-PIAT, described in particular details in WO2006/080849) or from a number of different amphiphilic block copolymers, including poly(ethylene oxide)-b-polybutadiene (PEO-b-PBD), poly(ethylene oxide)-b-polyethylethylene (PEO-b-PEE), poly(ethylene oxid)-polylactic acid (PEO-PLA), polystyrene-b-poly(ethylene oxide) (PS-b-PEO), poly(ethylene oxide)-b-poly(propylene oxide)-b-poly(ethylene oxide) (PEO-b-PPO-b-PEO) triblock copolymer, polystyrene-b-poly(acrylic acid) (PS-b-PAA), poly(2-methyloxazoline)-b-poly(dimethylsiloxane)-b-poly(2-methyloxazoline) (PMOXA-b-PDMS-b-PMOXA), etc. or from block copolymers of polyethylene oxide and polycaprolactone, e.g. comprising hydrophobic polycaprolactone, polylacticde, polyglycolide, or polymethylene carbonate polymer blocks used in combination with a corresponding polyethyleneoxide polymer block. Further the polymersome can be based upon an amphiphilic random copolymer consisting of a discrete polyethylene oxide block and a random hydrophobic polymer block in which there exists an oligocaprolactone component, and hydrophobic polylacticde, polyglycolide, or polymethylene carbonate oligomers.

Polypeptides usable for preparing the shell, cover, layer(s) or coating on the marker molecules of the cell- or virus simulating means are peptides having at least 5 and up to about 150 amino acids, preferably having 5 to 100 amino acids, more preferably having 15 to 45 amino acids, wherein it is preferred, but not required, that all of the charged residues in each motif be of the same charge. 4 charged amino acids is the preferred minimum for a motif size of 7, whereas one polypeptide may comprise several motifs.

The preferred motifs should not be too long to minimize secondary structure formation. Secondary structure decreases control of the physical structure of the polypeptides (see below) and the films made from them. Thus, an amino acid sequence motif should contain 5 to 15 contiguous amino acids and a polypeptide may comprise several motifs. Further, it is preferred that at least 4 positively-charged (basic) amino acids (Arg, His, or Lys) or at least 4 negatively-charged (acidic) amino acids (Glu or Asp) are present in each 7-residue motif at neutral pH. Combinations of positive and negative charges are disfavored in an effort to ensure a sufficiently high charge density at neutral pH. It is possible, however, that a motif containing both positive and negative amino acids could be useful for layer forming. For example, a slightly longer motif, say of 9 residues, could have 6 positively charged amino acids and 1 negatively charged amino acid. It is the magnitude of the net charge (i.e., the absolute value of the net charge) that is important— the overall peptide must be either sufficiently positively charged or sufficiently negatively charged at neutral pH. Preferred embodiments of the motifs, however, will contain only Glu or Asp or only Arg, His, or Lys as the charged amino acids (although other non-charged amino acids could, and ordinarily do, form part of the motifs), unless non-natural amino acids are admitted as acidic or basic amino acids.

Suitable polypeptides are e.g.:

```
                                                        (SEQ ID NO: 1)
Tyr Lys Cys Lys Gly Lys Val Lys Val Lys Cys Lys Gly Lys Val Lys

Val Lys Cys Lys Gly Lys Val Lys Val Lys Cys Lys Gly Lys Val Lys
and
                                                        (SEQ ID NO: 2)
Tyr Glu Cys Glu Gly Glu Val Glu Val Glu Cys Glu Gly Glu Val Glu Val Glu Cys Glu Gly Glu Val Glu Val Glu Cys Glu Gly Glu Val Glu.
```

The prior state of the art provides several types of spherical or regular or irregular shaped particles suitable for the present invention, if they are loaded with or comprising at least one type of a biomolecule with an at least partially pre-known sequence, preferably in a defined amount. In particular the layer(s), cover, coating or shell of the cell- or virus simulating means according to the present invention can be prepared as described in the below cited prior art.

US 2009/0253901 A1 describes the encapsulation of nucleic acids by either adsorption of nucleic acids to a preformed porous calcium carbonate template or co-precipitation of the nucleic acids with the calcium carbonate followed by providing several layers of polyelectrolytes on the surface of said nucleic acids comprising template by layer-by-layer technology. The calcium carbonate template thereafter might be dissolved or disaggregated, or it remains in the particle. The particles of this application comprising encapsulated nucleic acids can be used as an internal standard of the present invention.

WO99/47252 describes the preparation of nanocapsules and microcapsules by layer-wise polyelectrolyte self-assembly. The microcapsules described in this application can be used as a standard according to the present invention, if they are prepared to comprise a defined amount of marker molecules according to the present invention. Further the polyelectrolytes described in this application can be used to prepare a covering layer or coating on a defined amount of at least one type of marker molecules on a substrate, preferably a device as according to the invention.

WO99/47253 discloses the preparation of multilayer-coated particles and hollow shells via electrostatic self-assembly of nanocomposite mulitlayers on decomposable templates. Said particles comprising still the template or said shells wherein the template is decomposed can be used as the internal standard of the present invention, if a known amount of at least one marker molecule is contained. Further the polyelectrolytes described in this application can be used to prepare a covering layer or coating on a defined amount of at least one type of marker molecules on a substrate, preferably a device as according to the invention.

WO2007/031345 describes as well microcapsules prepared by layer-by-layer technique of polyelectrolytes on a template. These microcapsules are as well suitable for the present invention if they are prepared in a way that the comprise a defined amount of at least one marker molecule according to the present invention. Further the polyelectrolytes described in this application can be used to prepare a covering layer or coating on a defined amount of at least one type of marker molecules on a substrate, preferably a device as according to the invention.

WO2007/140402 describes the preparation of a coating prepared by the layer-by-layer technique from polyelectrolytes on a substrate. The layer(s), cover, coating or shell of the cell- or virus simulating means may also be prepared as described therein and the resulting beads, spheres, capsules or particles can be used according to the invention, if the are prepared to comprise a defined amount of at least one marker molecule of an at least partially pre-known sequence or comprising a labelling. Further the polyelectrolytes described in this application can be used to prepare a covering layer or coating on a defined amount of at least one type of marker molecules on a substrate, preferably a device as according to the invention.

WO2008/030253 explains the layer-by-layer coating of a substrate using selected polypeptides as polyelectrolytes. These polypeptides as well can be used the same way to prepare the layer(s), cover, coating or shell of the cell- or virus simulating means of the present invention.

WO2006/080849, WO2007/038763 and WO2008/060557 each describe polymersome preparations. The polymers used for preparing the polymersomes as well can be used to prepare the layer(s), cover, coating or shell of the cell- or virus simulating means of the present invention. Polymersomes prepared as comprising at least one type of marker molecules can be used in the present invention.

As mentioned above, if the cell- or virus-simulating means is used as an internal standard, said standard comprising at least one type of a marker is present during the whole treatment of the biological sample for biomolecule isolation, at least it is already present when the interesting cells or viruses are lysed. The standard can be either added to the cell or virus comprising sample to be present during the lysis of the sample and the following treatment, or the internal standard is representing a layer or coating on the inner wall of a device wherein the biological cell or virus containing sample is treated for biomolecule isolation. In the last mentioned embodiment the marker molecule of the internal standard is applied on an inner surface of said device and covered by at least one layer or a coating as described above.

Since the internal standard is present in the same sample as the biomolecule containing cells or viruses of interest, it is treated exactly the same way as the cells or viruses of interest. Accordingly, if the marker molecule(s) of the internal standard are released from the internal standard, biomolecules of similar cells or viruses as well are released under the applied conditions. Furthermore, the marker molecules of the internal standard in the further processing are treated the same way and under the same conditions as the biomolecules of the cells or viruses and accordingly the obtainable result of each treatment or processing step can be controlled by detecting the marker molecules of the internal standard.

Since the marker molecules of the cell- or virus-simulating means themselves are detectable or they have an at least partially pre-known sequence and/or a label, they are detectable by any suitable detection method known in the art, like e.g. specific amplification by PCR, sequence analysis, hybridization, blotting methods (northern, southern, western), dye or fluorescence detection or similar. The detection method is not limiting the invention.

The lysis of the cells or viruses and the according decomposing of the layer(s), cover, coating or shell of the cell- or virus-simulating means (further as well referred to as "lysis of the cell- or virus-simulating means") can be obtained by chemical or mechanical lysis or by a mixture of both.

If mechanical lysis is used to lyse the cells or viruses of interest, it is preferred that the cell- or virus-simulating means either comprises a porous template whereon the marker molecules are adsorbed or applied and covered/coated with layers of the above described assembling materials, or they doesn't comprise a template, but the marker molecules are contained in a core further comprising a liquid.

If chemical lysis is used to lyse the cells of interest, it is preferred that the cell- or virus-simulating means comprises a solid template, preferably having an essentially plain surface whereon the marker molecules are applied or adsorbed.

The layer(s), cover, coating or shell can be furthermore "tuned" or "designed" to resist for example a chemical lysis, but not a mechanical or vice versa, which is desirable if the biological cell comprising sample contains two types of cells or viruses, wherein only one of them is of interest. E.g. if a microorganism infection in a mammal should be detected, the sample comprises mammal tissue or blood cells and further microorganisms. The focus of interest are the microorganisms, however the biomolecules of the mammal cells are as well released by mechanical lysis. In such a case first the mammal cells are lysed by chemical lysis and the microorganisms (not lysed by chemical treatment) are separated and thereafter mechanically lysed. In such a case it is preferred that the cell- or virus-simulating means is not decomposed before the mechanical lysis is applied.

According to the present invention as well a composition is provided comprising the cell- or virus-simulating means of the present invention. Said composition comprises preferably the cell- or virus-simulating means in a defined amount so that it is possible to add a defined amount of the means to a sample, resulting in a defined amount of the marker molecule of the cell- or virus-simulating means in the sample. In a preferred embodiment the cell- or virus-simulating means may comprise 0.05 to 20% (w/w) of at least one type of a marker molecule, preferably 0.1 to 10%, more preferably 1 to 7%. For example a cell- or virus-simulating means may be prepared that it contains 5 µg nucleic acid of a pre-known sequence or having a label in 0.1 mg of the cell- or virus-simulating means (resulting in a 5% standard). The standard may be provided as a dispersion. The cell- or virus-simulating means preferably is dispersed in water or an aqueous solution. This allows a particular simple handling of the standard, e.g. for adding a defined amount of the marker molecule to a biological sample. If e.g. the cell- or virus-simulating means is contained with 1 mg/ml of the composition (as a dispersion) for example 10 µl may be added to the biological sample. Accordingly a predetermined amount of marker molecule(s) can be added to any sample by measuring the added amount of the dispersion.

The composition further may comprise at least one further component, preferably selected from buffering substance(s), a chaotropic agent, a detergent or any suitable component.

Further the invention provides a device for use in a biomolecule isolation method comprising at least one inner surface coming in contact with any biological cell material, virus or microorganism(s) during the isolation method and at least partial coating comprising at least one type of marker molecule(s). Said device is preferably an isolating device usable during a biomolecule isolation method, comprising on at least one of its inner surfaces coming in contact with any biological cell, virus or microorganism(s) comprising material a known amount of a marker molecule covered or coated with an assembling, preferably a self-assembling material as described above. Preferred examples of the device are: cup, a tube, a column, a microtiter plate, a multiwell plate, capped tubes prefilled with buffers and/or glassbeads or the like. Again, it is particularly preferred that the marker molecule(s) are provided in the device in a known amount.

The cell- or virus-simulating means, the composition or the device can be used in a method for the control of a deliberate release of an encapsulated or embedded marker molecule or compound comprised in a cell- or virus-simulating means according to the invention by (i) lysis of said means and (ii) detecting the marker molecule or compound. The cell- or virus-simulating means, the composition or the device can particularly be used for finding, defining, establishing and/or controlling the conditions suitable for effective biomolecule-release form a biological sample, preferably in a biomolecule release or isolation process. Furthermore the cell- or virus-simulating means, the composition or the device can be used to control and/or to estimate at least the success and/or the extent of breakage or lysis of a biological cell material, virus or any microorganism. Preferably the standard, composition or device can be used to control or estimate the success of any of the steps of a biomolecule purification and detection method, since the standard can be used in a known amount and the percentage of the recovered marker molecule it can be determined by aid of the pre-known sequence, the label or the other detectable marker of the marker molecule. Accordingly the standard, composition or device can be used in a "diagnostic chain" as a full process control.

The invention also provides a kit for isolation of at least one biomolecule of a biological cell, virus or microorganism comprising sample, comprising a cell- or virus-simulating means or a composition or a device as described above. The kit further may comprise e.g. a lysis buffer, a mechanical lysis device like e.g. glass beads, and/or a tool for detecting the marker molecule, the pre-known sequence or the label of the marker molecule of the cell- or virus-simulating means like e.g. PCR primer or a probe annealing to the pre-known sequence of a nucleic acid sequence of the cell- or virus-simulating means, or an antibody recognizing the pre-known sequence of a peptide or protein or the label of any marker molecule of the cell- or virus-simulating means. Further the kit preferably comprises instructions for carrying out at least one of the methods of the present invention.

FIGURES

FIG. 1: a poly(beta-amino ester)s as an example for the suitable polyelectrolytes.

Figure 2:
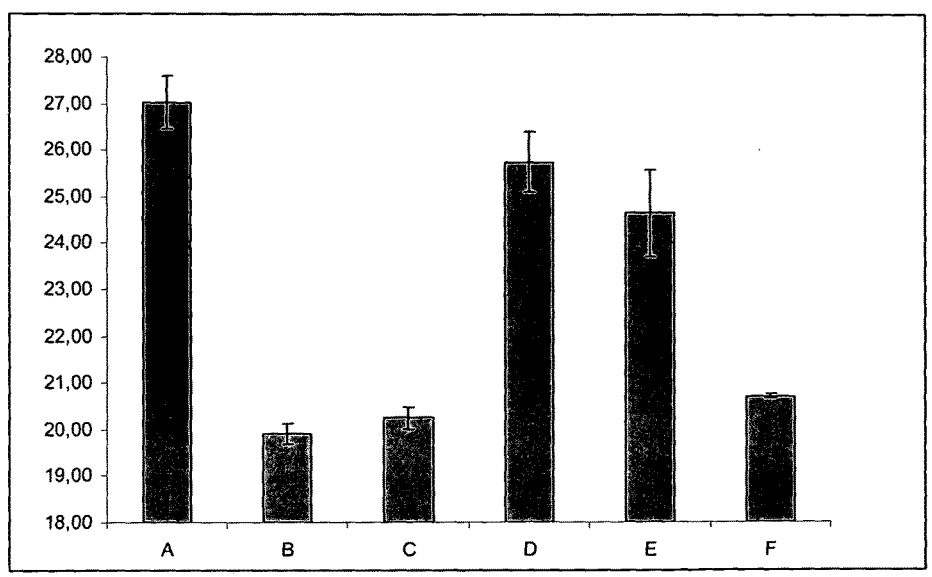

FIG. 2: Results (Ct values) of real time PCR analysis of DNA comprised in internal standard types. On the left side the internal standard comprised a silica core with a PB-12-5/PAH/DNA/(PAH/PSS)$_5$ coating without a final crosslinking (columns A, B and C), on the right side the internal standard comprised a silica core with a PB-12-5/PAH/DNA/(PAH/PSS)$_5$ coating with a final crosslinking (columns D, E and F). Said standards are differently treated before used in a PCR, either non-treated (A and D), chemically treated (B and E) or additionally mechanically treated (C and F), see Example 1.

Figure 3:
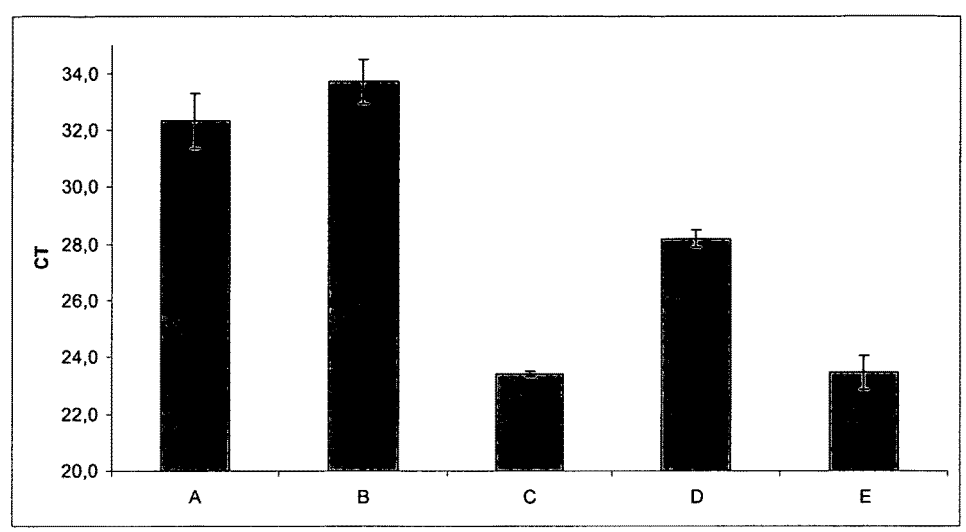

FIG. 3: Results of real time PCR analysis of DNA comprised in an internal standard with final crosslinking. Ct values of PCR of untreated internal standards (A) or supernatant of the untreated standard (B), after mechanical treatment (C) or chemical treatment (D) or after a combination of mechanical and chemical treatment (E) are shown, see Example 2

EXAMPLES

Example 1

A PCR product was encapsulated by layer-by-layer technique according to the method as described in WO99/47253. At first a silica core was loaded with a first layer of the polycation polyallylamin-hydrochloride (PAH), whereon the DNA of a PCR product was bound through absorption (5 µg DNA/100 µg beads). Thereafter in alternating order five layers each of the polycation PAH and the polyanion polystyrolsulfate (PPS) were applied on the DNA (in sum 10 layers). The surface of one portion of the particles was additionally crosslinked by means of crosslinking agent (portion 1), whereas the other portion remained without further treatment (portion 2).

For analysis the particles were either used directly as a sample in a PCR or alternatively the particles were previously applied to a DNA isolation by using the commercially available QIAamp UCP Pathogen Mini Kit with/without mechanical pretreatment. The lysis buffer contained 4,5M Guanidinthiocyanat, 20% Brij 58, 100 mM Tris, pH 8,0. Mechanical treatment was carried out by shaking the sample with glass beads (400 mg glass beads with a diameter of 400-625 µm are added to the 500 µl of particle solution and shaken for 10 min on a laboratory Vortexer at maximum speed). The results in FIG. 2 show that independent from the cross-linking only a weak signal (high ct amount) can be obtained by direct use of the particles in the PCR, i.e. all the particles are resistant against the extreme heat conditions in the PCR (columns A and D in FIG. 2). However, in case the particles are subjected to chemical lysis and thereafter the released DNA is purified, a visibly lower ct-amount can be noted (~7 ct amounts difference=~150 time amount DNA) at the not cross-linked particles (column B). An additional mechanical lysis didn't increase the obtainable DNA (column C). In case additionally cross-linked layers (portion 1) were applied on the outer LbL layers the particles rendered resistant against chemical lysis (column E) and the encompassed nucleic acid was only released by means of an additional mechanical lysis (column F).

Thus it is possible to adapt the properties of the control particles to the demands of lysis of the interesting biological sample and the required decomposition/purification procedure. Whereas particles of part 2 (without cross-linking) are suitable for the control of a chemical lysis e.g. for molecular-diagnostic detection of viruses, particles of part 1 (cross-linked) are suitable for monitoring the essential mechanical lysis of bacterial or fungal pathogens.

Example 2

For a further analysis of control particles of the invention also a PCR product was applied to a silica core (5 µg DNA/100 µg beads) and encapsulated by 12 layers PAH and PSS as described in WO 99/47253 and thereafter the surface was crosslinked with a crosslinking agent. If those particles (or the supernatant after centrifugation) are used as a sample in a real time PCR without any pretreatment (see FIG. 3), only very poor signals (very high ct values) can be notified (column A (=particles) and column B (=supernatant) in FIG. 3). These signals may represent a remainder of not encapsulated DNA in the samples. Such DNA can be removed for example by supplementary DNase treatment of the prepared particles. (Data available, but not shown). However, if the particles are mechanically lysed with glass beads (column C) (400 mg glass beads with a diameter of 400-625 µm are added to the 500 µl of particle solution and shaken for 10 min on a laboratory Vortexer at maximum speed) and thereafter the supernatant is analyzed in real time PCR, a significant release of the encapsulated DNA is shown (column C). When only chemical lysis (lysis conditions as in Example 1) is applied by means of chaotropic salts followed by DNA purification, only a very low amount of the DNA is released (column D). If mechanical lysis is combined with chemical lysis and DNA purification, once again maximum release of DNA is shown (column E).

The lysis behavior of these control particles thus is highly similar to the lysis behavior of microbial pathogens (gram-positive bacteria or fungi). These pathogens are also only lysed in a low amount by chemical lysis and have to be treated mechanically for complete lysis. Using the particles of the present invention as a control the success of a procedure of a complete (diagnostic) workflow can be controlled by defining an acceptable range of detection for the marker molecule encapsulated in the particles. If for example a mechanical lysis is not applied to a sample comprising bacteria and/or fungi, the control marker molecule would not be detectable in the required amount. This may serve as a sign that bacteria and fungi to be detected in the sample as well are not correctly decomposed.

The invention claimed is:

1. A cell- or virus-simulating artificial, solid object or article, comprising:
    a core and a shell,
    wherein the core comprises at least one type of marker molecules selected from the group consisting of nucleic acids, oligopeptides, polypeptides, proteins, biological cells, biological organisms, viruses, phages, or phage core particles, and wherein the shell covers and encloses all of the at least one type of molecules, and
    wherein the shell does not comprise a polypeptide.

2. The cell- or virus-simulating artificial, solid object or article according to claim 1, wherein the at least one type of marker molecules is selected from nucleic acids, oligopeptides, polypeptides, and proteins.

3. The cell- or virus-simulating artificial, solid object or article according to claim 1, wherein the at least one type of marker molecules is DNA having a pre-known sequence of at least 10 bp.

4. The cell- or virus-simulating artificial, solid object or article according to claim 1, wherein the cell- or virus-simulating artificial, solid object or article is on an inner surface of a device,
    the at least one type of marker molecules is applied on said inner surface, and
    a coating or layer covers all of the marker molecule(s) on the inner surface.

5. The cell- or virus-simulating artificial, solid object or article according to claim 1, wherein the cell- or virus-simulating artificial, solid object or article is represented by a bead, capsule, sphere or particle providing at least one of the following features:
    (i) size of 10 nm to 1 mm, 100 nm to 100 μm, 0.5 to 50 μm, or 1 to 10 μm;
    (ii) the core further comprises a liquid or an inorganic or organic template, and is liquid, solid or porous; and
    (iii) the coating or shell covering or the marker molecules comprises an assembling material selected from polyelectrolytes, organic polymers, polypeptides, and phospholipids.

6. A method for isolating and/or analysing biomolecules from a virus-, cell- or microorganism(s)-containing biological sample, comprising:
    lysing the biological sample in the presence of or in parallel with the cell- or virus-simulating artificial, solid object or article according to claim 1.

7. A method for the control of a deliberate release of an encapsulated or embedded marker molecule comprised in the cell- or virus-simulating artificial, solid object or article of claim 1, comprising:
    lysing the cell- or virus-simulating artificial, solid object or article, and
    detecting the at least one type of marker molecules.

8. The method according to claim 7, wherein the method is used for finding, defining, establishing and/or controlling the conditions suitable for effective biomolecule release from a biological sample.

9. The method according to claim 8, wherein the method is used for finding, defining, establishing and/or controlling the conditions suitable for effective biomolecule release from a biological sample in a biomolecule release or isolation process.

10. A method for the control and/or estimation of the success and/or extent of breakage or lysis of a biological cell material, virus or microorganism(s), comprising:
    lysing the biological cell material, virus or microorganism(s) in the presence of or in parallel with the cell- or virus-simulating artificial, solid object or article according to claim 1, and
    detecting the marker molecule.

11. A method for deliberate release of a marker molecule or a biomolecule into a liquid sample, comprising:
    chemically or mechanically lysing the cell- or virus-simulating artificial, solid object or article of claim 1 in a liquid sample, thereby releasing the marker molecule or the biomolecule into the liquid sample.

12. The method according to claim 6, wherein the cell- or virus-simulating artificial, solid object or article
    is added to the biological sample,
    is present in a device used during the isolation of the biomolecules from the biological sample, or
    is used separately from the biological sample in a parallel process.

13. The method according to claim 12, wherein the cell- or virus-simulating artificial, solid object or article
    is added to the biological sample,
    is present in a device used during the isolation of the biomolecules from the biological sample, or
    is used separately from the biological sample in a parallel process that is carried out in the same way.

14. The method according to claim 6, wherein the marker molecules of the cell- or virus-simulating artificial, solid object or article are released during the isolation of the biomolecules from the biological sample, and are isolated together or in parallel with the biomolecules of the biological sample.

15. A composition for lysis of a biological cell material, virus or microorganism comprising the cell- or virus-simulating artificial, solid object or article according to claim 1.

16. The composition according to claim 15, further comprising at least one component selected from water, buffering substance(s), a chaotropic agent, and a detergent.

17. An isolation device for use in a biomolecule isolation method, comprising: on at least one inner surface coming in contact with a biological cell material, virus or microorganism(s) during the isolation method, a cell- or virus-simulating artificial, solid object or article of claim 1.

18. The isolation device according to claim 17, wherein the at least one type of marker molecules is labelled by a dye, a fluorescent dye, a dye developing compound, an antigen, an antibody, green fluorescent protein (GFP), or radioactivity.

19. The isolation device according to claim 17, wherein the at least one of the inner surface(s) is at least partially coated with a coating comprising a first layer comprising the marker molecule(s) and at least one further layer covering the marker molecule(s).

20. The isolation device according to claim 19, wherein said device is selected from a cup, a tube, a column, a microtiter plate, a multiwell plate, and cups/tubes prefilled with buffers and/or glass beads.

21. A kit for isolating biomolecules from a biological sample containing cells, virus(es) or a microorganism, comprising a cell- or virus-simulating artificial, solid object or article of claim 1.

22. The kit according to claim 21, further comprising at least one of
    (a) a lysis buffer,
    (b) a mechanical lysis device, and
    (c) a tool for detection of the marker molecule.

23. The cell- or virus-simulating artificial, solid object or article of claim 1, wherein the at least one type of marker molecules is selected from biological cells, biological organisms, viruses, and phages or phage core particles.

24. The cell- or virus-simulating artificial, solid object or article of claim 1, wherein the at least one type of marker molecules is labeled by a dye, a fluorescent dye, a dye-developing compound, green fluorescent protein (GFP), radioactivity, an antigen, or an antibody.

25. The cell- or virus-simulating artificial, solid object or article of claim 24, wherein the at least one type of marker molecules is linked to green fluorescent protein (GFP).

26. The cell- or virus-simulating artificial, solid object or article of claim 1, wherein the at least one type of marker molecules is selected from nucleic acids or polypeptides having a pre-known sequence.

27. The cell- or virus-simulating artificial, solid object or article of claim 1, wherein the shell comprises a poly(beta-amino ester).

* * * * *

SEQUENCE LISTING

```
<160> NUMBER OF SEQ ID NOS: 2

<210> SEQ ID NO 1
<211> LENGTH: 32
<212> TYPE: PRT
<213> ORGANISM: Homo sapiens

<400> SEQUENCE: 1

Tyr Lys Cys Lys Gly Lys Val Lys Val Lys Cys Lys Gly Lys Val Lys
1               5                   10                  15

Val Lys Cys Lys Gly Lys Val Lys Val Lys Cys Lys Gly Lys Val Lys
            20                  25                  30

<210> SEQ ID NO 2
<211> LENGTH: 32
<212> TYPE: PRT
<213> ORGANISM: Homo sapiens

<400> SEQUENCE: 2

Tyr Glu Cys Glu Gly Glu Val Glu Val Glu Cys Glu Gly Glu Val Glu
1               5                   10                  15

Val Glu Cys Glu Gly Glu Val Glu Val Glu Cys Glu Gly Glu Val Glu
            20                  25                  30
```